United States Patent
Inoue et al.

(10) Patent No.: US 6,515,165 B1
(45) Date of Patent: Feb. 4, 2003

(54) PROCESS FOR PRODUCING T-BUTYL ESTERS OF BRIDGED-RING POLYCARBOXYLIC ACIDS

(75) Inventors: Keizo Inoue, Himeji (JP); Shinya Nagano, Himeji (JP); Tomohide Ina, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/889,882

(22) PCT Filed: Nov. 21, 2000

(86) PCT No.: PCT/JP00/08182

§ 371 (c)(1),
(2), (4) Date: Jul. 24, 2001

(87) PCT Pub. No.: WO01/38286

PCT Pub. Date: May 31, 2001

(30) Foreign Application Priority Data

Nov. 24, 1999 (JP) .............................. 11-333484

(51) Int. Cl.$^7$ .............................. C07C 69/74

(52) U.S. Cl. ...................... 560/127; 585/352

(58) Field of Search ............... 560/127; 585/352

(56) References Cited

U.S. PATENT DOCUMENTS 4,931,584 A * 6/1990 Bru-Magniez et al.
6,143,465 A * 11/2000 Choi

FOREIGN PATENT DOCUMENTS

| JP | 51-138665 | * | 11/1976 |
| JP | 52-3046 | * | 1/1977 |
| JP | 58-110538 | * | 7/1983 |

OTHER PUBLICATIONS

Eremenko et al, Russian Chemical Bulletin, vol. 47, No. 3, 1998, pp. 441–446.*

(List continued on next page.)

Primary Examiner—Alan L. Rotman
Assistant Examiner—Hector M Reyes
(74) Attorney, Agent, or Firm—Birch, Stewart, Kolasch & Birch, LLP

(57) ABSTRACT

In a process of the present invention for producing a bridged cyclic polycarboxylic acid t-butyl ester, a bridged cyclic polycarboxylic halide of following Formula (1):

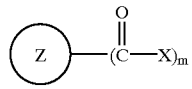

(1)

(wherein ring Z is a bridged cyclic carbon ring; X is a halogen atom; and m denotes an integer of 2 or more, where ring Z may have a substituent) is allowed to react with t-butyl alcohol or its alkali metal salt to thereby yield an ester of following Formula (2):

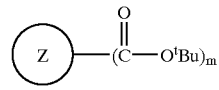

(2)

(wherein $^t$Bu is a t-butyl group; and ring Z and m have the same meanings as defined above.) This process can commercially efficiently produce a bridged cyclic polycarboxylic acid t-butyl ester. The compound of Formula (1) can be prepared by allowing a bridged cyclic polycarboxylic acid of following Formula (3):

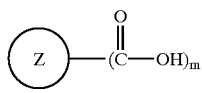

(3)

(wherein ring Z is a bridged cyclic carbon ring; and m denotes an integer of 2 or more, where ring Z may have a substituent) to react with a halogenating agent.

6 Claims, 1 Drawing Sheet

OTHER PUBLICATIONS

Eremanko et al. Russian Chemical Bulletin, vol. 47, No. 3, 1998, pp. 441–446.*

Braun et al, J. Prakt Chem. 339 (8), 1997, 339 (8) pp.709–712.*

L.T. Eremenko et al., Russ. Chem. Bull., 1998, vol. 47, No. 3, PP441–446.*

* cited by examiner

PROCESS FOR PRODUCING T-BUTYL ESTERS OF BRIDGED-RING POLYCARBOXYLIC ACIDS

This application is the national phase under 35 U.S.C. §371 of PCT International Application No. PCT/JP00/08182 which has an International filing date of Nov. 21, 2000, which designated the United States of America and was not published in English.

TECHNICAL FIELD

The present invention relates to a process for producing a bridged cyclic polycarboxylic acid t-butyl ester that is useful, for example, as a sensitizer for resists, and to a novel norbornanepolycarboxylic acid t-butyl ester compound.

BACKGROUND ART

Adamantanedicarboxylic acid t-butyl esters and other bridged cyclic polycarboxylic acid t-butyl esters each have a polycyclic alicyclic group that improves etching resistance, and have a t-butoxycarbonyl group that is decomposed by action of an acid generated from a photosensitive acid generator to yield a carboxyl group. Accordingly, these compounds receive attention as sensitizers or dissolution inhibitors for photoresists. The addition of such bridged cyclic polycarboxylic acid t-butyl esters to resist resin compositions can yield sharp patterns. When the bridged cyclic polycarboxylic acid t-butyl esters are used as, for example, sensitizers for photoresists, they must be highly pure containing less impurities such as metallic components or coloring substances, in order to avoid deterioration of the properties of resists.

The adamantanedicarboxylic acid t-butyl esters and other bridged cyclic polycarboxylic acid t-butyl esters have been conventionally produced by allowing bridged cyclic polycarboxylic acids to react with isobutylene in the presence of an acid catalyst. This process, however, only achieves a very low yield of about 20% and is very insufficient as a commercial production process. Additionally, no process that can yield the bridged cyclic polycarboxylic acid t-butyl esters with high purity has been known.

Furthermore, conventional bridged cyclic polycarboxylic acid t-butyl esters are not always satisfactory as the sensitizers or dissolution inhibitors for photoresists, and demands have been made to provide substances with higher properties.

DISCLOSURE OF INVENTION

Accordingly, an object of the present invention is to provide a process that can commercially efficiently produce a bridged cyclic polycalrboxylic acid t-butyl ester.

Another object of the present invention is to provide a process that can easily produce a high-quality bridged cyclic polycarboxylic acid t-butyl ester containing less impurities such as metallic components.

Yet another object of the present invention is to provide a novel bridged cyclic polycarboxylic acid t-butyl ester that is useful, for example, as a sensitizer or dissolution inhibitor for photoresists.

After intensive investigations to achieve the above objects, the present inventors have found that the reaction of a bridged cyclic polycarboxylic halide with t-butyl alcohol or its alkali metal salt can produce a corresponding ester in a surprisingly very high yield, in spite of the bulkiness of the two components, and that a specific treatment of the reaction product can produce a highly pure bridged cyclic polycarboxylic acid t-butyl ester. Additionally, the present inventors have found a novel bridged cyclic polycarboxylic acid t-butyl ester during the investigations. The present invention has been accomplished based on these findings.

Specifically, the present invention provides a process for producing a bridged. cyclic polycarboxylic acid t-butyl ester, the process including the step of allowing a bridged cyclic polycarboxylic halide represented by following Formula (1):

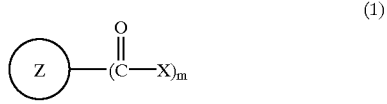

(1)

(wherein ring Z is a bridged cyclic carbon ring; X is a halogen atom; and m denotes an integer of equal to or more than 2, where ring Z may have a substituent) to react with t-butyl alcohol or its alkali metal salt to thereby yield an ester represented by following Formula (2):

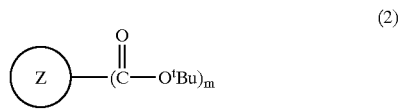

(2)

(wherein $^t$Bu is a t-butyl group; and ring Z and m have the same meanings as defined above.)

In this production process, a bridged cyclic polycarboxylic acid represented by following Formula (3):

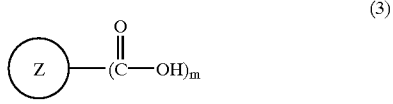

(3)

(wherein ring Z is a bridged cyclic carbon ring; and m denotes an integer of equal to or more than 2; where ring Z may have a substituent) may be allowed to react with a halogenating agent to thereby form the bridged cyclic polycarboxylic halide represented by Formula (1), and this bridged cyclic polycarboxylic halide may be allowed to react with t-butyl alcohol or its alkali metal salt.

The production process may include at least an adsorption treatment step of subjecting a reaction product to an adsorption treatment with an adsorbent, which reaction product is of the bridged cyclic polycarboxylic halide represented by Formula (1) with t-butyl alcohol or its alkali metal salt.

Furthermore, the production process may include at least a crystallization step of subjecting a reaction product to crystallization using solvent mixture of water and a water-miscible solvent, which reaction product is of the bridged cyclic polycarboxylic halide represented by Formula (1) with t-butyl alcohol or its alkali metal salt.

In the production process, the reaction product of the bridged cyclic polycarboxylic halide represented by Formula (1) with t-butyl alcohol or its alkali metal salt may be purified by successively subjecting to (A) a washing step of washing the reaction product with water, (B) an adsorption treatment step of subjecting the reaction product to an adsorption treatment with an adsorbent, and (C) a crystallization step to thereby yield a bridged cyclic polycarboxylic acid t-butyl ester.

Ring Z in Formula (1) includes, for example, bicyclic, tricyclic or tetracyclic bridged cyclic carbon rings such as an adamantane ring or norbornane ring.

In addition and advantageously, the present invention provides a norbornanepolycarboxylic acid t-butyl ester compound represented by following Formula (4):

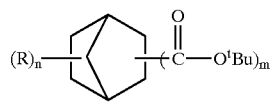
(4)

(wherein R is a substituent bonded to norbornane ring; n denotes an integer from 0 to 5, where substituents R may be different from each other when n is equal to or more than 2; $^tBu$ is a t-butyl group; and m denotes an integer equal to or more than 2.)

BEST MODE FOR CARRYING OUT THE INVENTION

Figure 1:
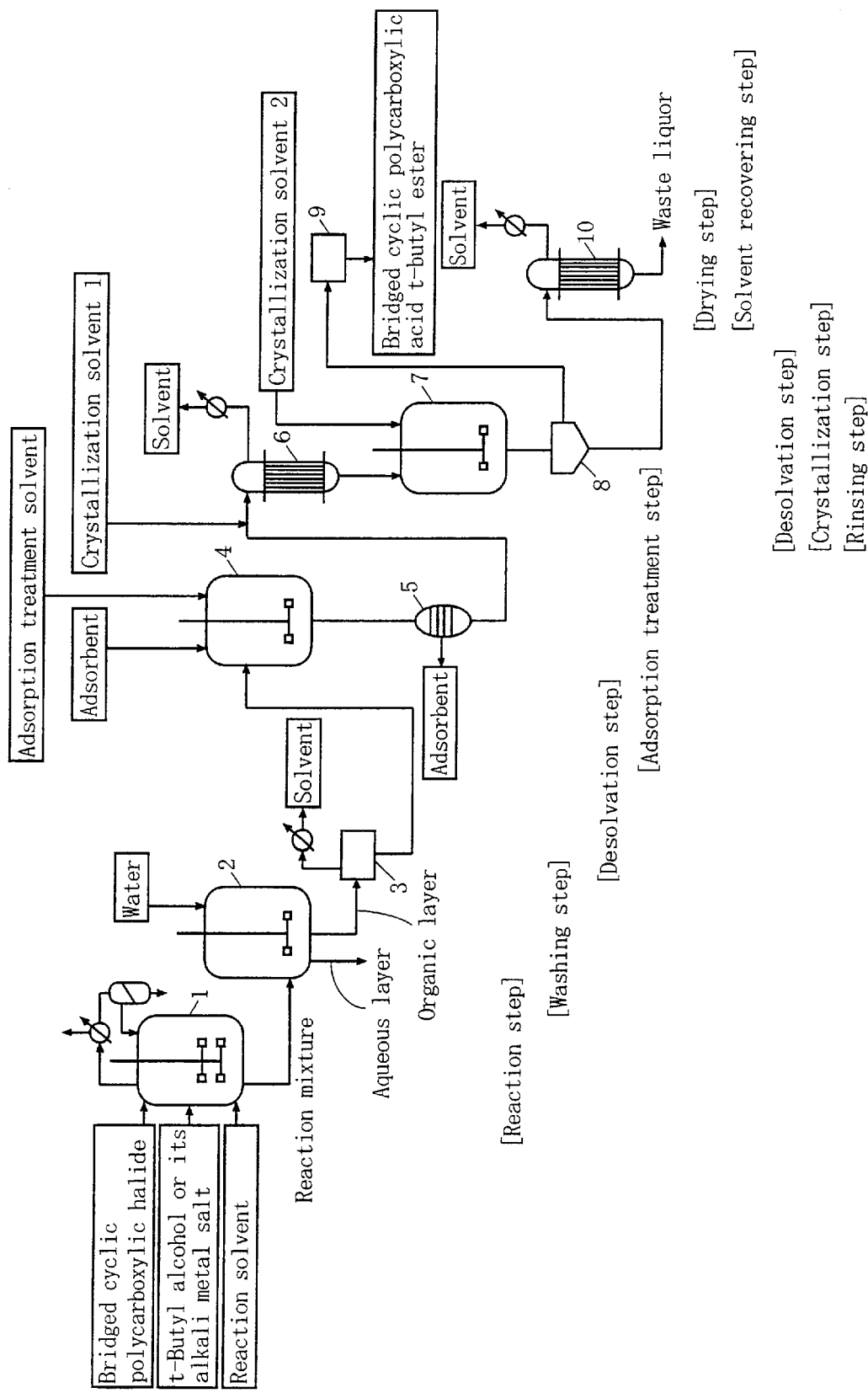
FIG. 1 is a production process chart showing an embodiment of the process of the present invention.

In the invented production process, ring Z is a bridged cyclic carbon ring. Such bridged cyclic carbon rings include, but are not specifically: limited to, perhydronaphthalene ring (decalin ring), perhydroanthracene ring, perhydrophenanthrene ring, perhydroacenaphthene ring, perhydrophenalene ring, perhydrofluorene ring, perhydroindene ring, isdbornane ring, pinane ring, norpinane ring, bornane ring, norbornane ring, norbornene ring, bicyclo[2.2.2] octane ring, adamantane ring, tricyclo[5.2.1.0$^{2,6}$] decane ring, tetracyclo [4.4.0.1$^{2,5}$.1$^{7,10}$] dodecane ring, and other bridged cyclic carbon rings each having from about two to about four rings. These bridged cyclic carbon rings may each have one or more (e.g., from about one to about five) substituents.

Such substituents :include, but are not limited to, halogen atoms (fluorine, chlorine, bromine or iodine atom), alkyl groups (e.g., methyl, ethyl, isopropyl, and other $C_1$–$C_4$ alkyl groups), cycloalkyl groups, aryl groups (e.g., phenyl group and naphthyl group), hydroxyl group, hydroxymethyl group, alkoxy groups (e.g., methoxy, ethoxy, isopropoxy, and other $C_1$–$C_4$ alkoxy groups), acyloxy groups (e.g., acetyloxy, propionyloxy group, (meth) acryloyloxy group, and other $C_2$–$C_4$ aliphatic acyloxy groups), carboxyl group, carboxymethyl group, alkoxycarbonyl groups (e.g., methoxycarbonyl, ethoxycarbonyl, propoxycarbonyl, and other $C_1$–$C_4$ alkoxy-carbonyl groups), cycloalkyloxycarbonyl groups (e.g., cyclohexyloxycarbonyl group), aryloxycarbonyl groups (e.g., phenyloxycarbonyl group), aralkyloxycarbonyl groups (e.g., benzyloxycarbonyl group), substituted or unsubstituted carbamoyl groups (e.g., carbamoyl group; and methylcarbamoyl, dimethylcarbamoyl, diethylcarbamoyl, and other mono- or di-$C_1$–$C_4$ alkylcarbamoyl groups), acyl groups (e.g., acetyl, propionyl, and other $C_2$–$C_6$ aliphatic acyl groups, and specifically $C_2$–$C_4$ aliphatic acyl groups), oxo group, substituted or unsubstituted amino groups (e.g., amino group; and methylamino, ethylamino, propylamino, dimethylamino, diethylamino, and other mono- or di-$C_1$–$C_4$ alkylamino groups), cyano group, and nitro group. The hydroxyl group, hydroxymethyl group, carboxyl group, carboxymethyl group, amino group and the like may be protected by a conventional protective group.

Among them, preferred substituents include, for example, halogen atoms, $C_1$–$C_4$ alkyl groups, oxo group, hydroxyl group which may be protected by a protective group, and carboxyl group which may be protected by a protective group.

In Formula (1), the halogen atoms represented by X include, for example, chlorine, bromine, and iodine atoms. The numeral m denotes an integer of equal to or more than 2, and is preferably an integer from 2 to 4.

The alkali metals in alkali metal salts of t-butyl alcohol include, for example, lithium, sodium, and potassium. Preferred alkali metals are sodium or potassium, of which sodium is typically preferred.

The reaction (a dehydrohalogenation reaction or desalting reaction) of the bridged cyclic polycarboxylic halide represented by Formula (1) with t-butyl alcohol or its alkali metal salt is generally performed in an organic solvent. Such organic solvents may be any solvents as far as they do not adversely affect the reaction, and include, for example, hexane, octane, and other aliphatic hydrocarbons; benzene, toluene, xylene, and other aromatic hydrocarbons; cyclohexane and other alicyclic hydrocarbons; N,N-dimethylformamide (DMF), N,N-dimethylacetamide, and other amides; chloroform, dichloromethane, dichloroethane, carbon tetrachloride, chlorobenzene, trifluoromethylbenzene, and other halogenated hydrocarbons; ethyl acetate, butyl acetate, and other esters; and mixtures of these solvents.

The amount of t-butyl alcohol or its alkali metal salt is, for example, from about 0.8 to about 1.5 moles relative to 1 mole of —C(=O)X group of the bridged cyclic polycarboxylic halide represented by Formula (1).

When t-butyl alcohol is used as the reactant, the reaction is generally performed in the presence of a base. Such bases include, but are not limited to, triethylamine, pyridine, and other organic bases. The amount of the base is, for example, from about 1 to about 1.5 moles relative to 1 mole of —C(=O)X group of the bridged cyclic polycarboxylic halide represented by Formula (1). The base can be used in large excess.

The reaction temperature of the dehydrohalogenation reaction or desalting reaction (esterification reaction) is, for example, from about –20° C. to about 100° C., and preferably from about –10° C. to about 50° C. The reaction can be performed in any of a batch system, semi-batch system and continuous system.

After the completion of the reaction, the formed bridged cyclic polycarboxylic acid t-butyl ester can be separated and purified, for example, by a separation and purification means such as filtration, concentration, distillation, extraction, crystallization, washing (cleaning), recrystallization, adsorption, or column chromatography, or a combination of these means.

To obtain a highly pure bridged cyclic polycarboxylic acid t-butyl ester, the :purification step should preferably include at least one step of an adsorption treatment step and a crystallization step. In the adsorption treatment step, the reaction product of the bridged cyclic polycarboxylic halide of Formula (1) with t-butyl alcohol or its alkali metal salt is subjected to an adsorption treatment with an adsorbent, and in the crystallization step, the reaction product of the bridged cyclic polycarboxylic halide of Formula (1) with t-butyl alcohol or its alkali metal salt is subjected to crystallization using a solvent mixture of water and a water-miscible solvent. Additionally, the reaction product should be preferably purified by successively subjecting the same to (A) a washing step of washing with water, (B) an adsorption treatment step of subjecting the reaction product to an adsorption treatment with an adsorbent, and (C) a crystallization step.

[Washing Step (A)]

The reaction product (reaction mixture) may be subjected to an adsorption treatment step as intact, but is preferably subjected to a washing step (cleaning step) (A) of washing the same with water prior to the adsorption treatment step. The washing liquid for use in the washing step may be any liquid, as far as it contains at least water. This washing treatment can efficiently remove salts and other water-soluble impurities from the reaction mixture. The amount of the washing liquid is, for example, from about 10 to about 200 parts by weight, and preferably from about 20 to about 100 parts by weight, relative to 100 parts by weight of the reaction mixture to be washed. A temperature in the washing operation is, for example, from about 10° C. to about 100° C. The washing operation can be performed by a known or conventional technique such as a batch system, continuous system or multistage system.

[Adsorption Treatment Step (B)]

In the adsorption treatment step (B), the reaction mixture or the resulting washed mixture obtained in the washing step (A) is subjected to solvent replacement according to necessity, and is then subjected to an adsorption treatment. The adsorption treatment technique is not specifically limited as far as it can remove impurities from the reaction product, and is preferably a treatment using at least one adsorbent selected from among activated carbon, chelating resins, chelating fibers, and zeta-potential membranes. Alternatively, a treatment using silica gel as the adsorbent is also preferable.

Two or more treatment technique may be used in combination in the adsorption treatment. The combination use of two or more treatment techniques can yield a product with a further higher purity. Such a combination of two or more treatment techniques includes the combination of at least one treatment technique selected from activated carbon treatment and silica gel treatment, with at least one treatment technique selected from chelating resin treatment, chelating fiber treatment and zeta-potential membrane treatment. In the combination use of two or more treatment techniques, the treatment can be performed in a single stage or in stages.

The solvent replacement can be performed, for example, by removing the reaction solvent from the reaction mixture or the washed mixture obtained in the washing step (A) by distillation, and adding a solvent for use in the adsorption treatment. In the solvent replacement, the reaction solvent is not necessarily completely removed, and it is also efficacious to concentrate the reaction mixture or washed mixture from about 4 to about 15 times. The removed reaction solvent can be reused.

Activated carbons for use in the activated carbon treatment are not specifically limited and any of gas-activated carbons and chemically activated carbons can be used. The origin of the activated carbon is not specifically limited, and any activated carbon can be used, such as activated carbons derived from vegetable materials such as wood, sawdust, shells of fruits, and carbonized shells of fruits; activated carbons derived from mineral materials such as peat, lignite, brown coal, coke, coal-tar pitch, and petroleum pitch; and activated carbons derived from synthetic resin materials such as phenol resins and acrylic resins. The shape of the activated carbon is also not specifically limited and may be any shape such as powdery, granular, or fibrous shape. The specific surface area of the activated carbon is, for example, from about 10 to about 3000 $m^2/g$.

The solution to be treated with activated carbon is not specifically limited as far as it is a solution. The solvent for use in the solution to be treated with activated carbon is preferably an alcohol such as methanol or ethanol, for more effective removal of impurities. The concentration of the bridged cyclic polycarboxylic acid t-butyl ester in the solution to be treated with activated carbon can be appropriately selected within a range not deteriorating treatment efficiency and workability and is generally from about 1 to about 50% by weight, and preferably from about 5 to about 30% by weight. When an alcohol such as methanol is used as the solvent in the activated carbon treatment, the amount of the alcohol is, for example, from about 200 to about 1000 parts by weight relative to 100 parts by weight of the bridged cyclic polycarboxylic acid t-butyl ester. The amount of the activated carbon can be appropriately selected in consideration of treatment efficiency and workability, and is, for example, from about 5 to about 1000 parts by weight, and preferably from about 10 to about 100 parts by weight, relative to 100 parts by weight of the bridged cyclic polycarboxylic acid t-butyl ester in the solution to be treated.

The activated carbon treatment may be performed at a temperature of, for example, from about 10° C. to about 150° C. The activated carbon treatment can be performed in a known manner such as a batch system, continuous system, fixed bed system, or fluidized bed system. The activated carbon treatment can mainly remove coloring components efficiently to thereby easily yield a bridged cyclic polycarboxylic acid t-butyl ester with satisfactory hue. Such a bridged cyclic polycarboxylic acid t-butyl ester with less degree of coloring is very useful, for example, as a sensitizer or dissolution inhibitor for photoresists.

Chelating resins for use in the chelating resin treatment are not specifically limited as far as they are resins having a functional group that can form a chelate with a metal. Typical examples thereof include iminodiacetic acid type chelating resins and polyamine type chelating resins. The ion exchange capacity of the chelating resin is not specifically limited and is, for example, from about 0.1 to about 2 mol/l.

The solution to be treated with chelating resin is not specifically limited as far as it is a solution. The solvent for use in the solution to be treated with chelating resin is preferably an alcohol such as methanol or ethanol or an ester such as ethyl acetate or butyl acetate, for more effective removal of impurities. The concentration of the bridged cyclic polycarboxylic acid t-butyl ester in the solution to be treated with chelating resin can be appropriately selected within a range not deteriorating treatment efficiency and workability, and is generally from about 1 to about 50% by weight, and preferably from about 5 to about 30% by weight. The amount of the chelating resin can be appropriately selected in consideration of, for example, treatment efficiency and workability and is, for example, from about 1000 moles to about 100000 moles in terms of exchange groups, relative to 1 mole of metals in the solution to be treated.

The chelating resin treatment is performed at a temperature of, for example, from about 10° C. to about 150° C. The chelating resin treatment can be performed in a known manner such as a batch system, continuous system, fixed bed system or fluidized bed system. The chelating resin treatment can mainly remove trace metallic components (e.g., Fe, Al) efficiently. The resulting bridged cyclic polycarboxylic acid t-butyl ester treated with chelating resin can be advantageously used as a sensitizer or dissolution inhibitor for photoresists.

Chelating fibers for use in the chelating fiber treatment are not specifically limited as far as they are natural fibers carrying a chelating functional group (e.g., an iminodiacetic acid type resin) fixed thereto through a chemical bond, and typical examples thereof include chelating fibers composed of cellulose as a base (e.g., one available from Chelest Corporation under the trade name of "Chelest Fiber").

The solution to be treated with chelating fiber is not specifically limited as far as it is a solution. Preferred solvents for use in the solution to be treated for more effective removal of impurities include, for example, methanol, ethanol, isopropyl alcohol, octanol, and other alcohols; ethyl acetate, butyl acetate, and other esters; toluene, and other aromatic hydrocarbons; hexane, heptane, and other aliphatic hydrocarbons; methylene chloride, 1,2-dichloroethane, and other halogenated hydrocarbons; and tetrahydrofuran and other ethers. The concentration of the bridged cyclic polycarboxylic acid t-butyl ester in the solution to be treated with chelating fiber can be appropriately selected within a range not deteriorating treatment efficiency and workability, and is generally from about 1 to about 50% by weight, and preferably from about 5 to about 30% by weight. The amount of the chelating fiber can be appropriately selected in consideration of, for example, treatment efficiency and workability.

The chelating fiber treatment is performed at a temperature of, for example, from about 10° C. to about 150° C. The chelating fiber treatment can be performed in a known manner such as a batch system, continuous system, fixed bed system or fluidized bed system. The chelating fiber treatment can mainly remove trace metallic components (e.g., Fe, Al) efficiently.

The zeta-potential membrane treatment is performed by allowing the solution to be treated to pass through a zeta-potential membrane. Such zeta-potential membranes for use in the zeta-potential membrane treatment are not specifically limited as far as they are filtration membranes to that can adsorb fine particles by action of zeta-potential, and include, for example, a zeta-potential membrane available from AMF Cuno under the trade name of "ZETA-PLUS". The zeta-potential membrane may be composed of, for example, a resin, cellulose, perlite, diatomaceous earth, or glass.

Solvents for use in the solution to be treated with zeta-potential membrane are not specifically limited, and typical examples thereof include methanol, ethanol, and other alcohols; ethyl acetate, butyl acetate, and other esters; toluene, xylene, and other aromatic hydrocarbons. The concentration of the bridged cyclic polycarboxylic acid t-butyl ester in the solution to be treated with zeta-potential membrane can be appropriately selected within a range not deteriorating treatment efficiency and workability, and is generally from about 1 to about 50% by weight, and preferably from about 5 to about 30% by weight.

The amount of the solution to be treated is, for example, from about 1 to about 30 kg per 1 $m^2$ of zeta-potential membrane. The treatment rate is, for example, from about 0.02 to about 2 $m^3/m^2$/hour.

The zeta-potential membrane treatment is performed at a temperature of, for example, from about 10° C. to about 150° C. The zeta-potential membrane treatment can mainly remove trace metallic components (e.g., Fe, Al) efficiently. The resulting bridged cyclic polycarboxylic acid t-butyl ester treated with zeta-potential membrane can be advantageously used as a sensitizer or dissolution inhibitor for photoresists.

Silica gels for use, in the silica gel treatment are not specifically limited. The solution to be treated with silica gel is not specifically limited as far as it is a solution. As the solvents, similar solvents to those in the solution to be treated with chelating fiber can be employed. The concentration of the bridged cyclic polycarboxylic acid t-butyl ester in the solution to be treated with silica gel can be appropriately selected within a range not deteriorating treatment efficiency and workability, and is generally from about 1 to about 50% by weight, and preferably from about 5 to about 30% by weight. The amount of the silica gel can be appropriately selected in consideration of, for example, treatment efficiency and workability.

The silica gel treatment is performed at a temperature of, for example, from about 10° C. to about 150° C. in a known manner such as batch system, continuous system, fixed bed system, or fluidized bed system. The silica gel treatment can efficiently remove high-boiling organic substances and coloring components. The resulting bridged cyclic polycarboxylic acid t-butyl ester with much less content of high-boiling organic substances is useful as a sensitizer or dissolution inhibitor for photoresists.

[Crystallization Step (C)]

The reaction product is generally subjected to crystallization step (C) after the adsorption treatment step (B). In the crystallization step (C), the bridged cyclic polycarboxylic acid t-butyl ester is crystallized from the adsorbed solution obtained in the adsorption treatment step (B) (where necessary after solvent replacement). In this connection, the reaction product (reaction mixture) may be directly subjected to the crystallization step (C) as intact, or the washed solution obtained in the washing step (A) may be subjected to the crystallization step (C).

Solvents for use in crystallization include, but are not limited to, benzene, toluene, xylene, ethylbenzene, and other aromatic hydrocarbons; hexane, heptane, octane, and other aliphatic hydrocarbons; cyclohexane and other alicyclic hydrocarbons; carbon tetrachloride, chloroform, dichloromethane, 1,2-dichioroethane, trifluoromethylbenzene, chlorobenzene, and other halogenated hydrocarbons; methanol, ethanol, isopropyl alcohol, butanol, and other alcohols; acetone, methyl ethyl. ketone, and other ketones; methyl acetate, ethyl acetate, isopropyl acetate, butyl acetate, ethyl benzoate, and other esters; acetonitrile, propionitrile, benzonitrile, and other nitrites; diethyl ether, diisopropyl ether, t-butyl methyl ether, dibutyl ether, dimethoxyethane, anisole, dioxane, tetrahydrofuran, and other chain or cyclic ethers; N,N-dimethylflormamide, N,N-dimethylacetamide, and other aprotic polar solvents; carbon disulfide; water; and mixtures of these solvents.

Preferred crystallization solvents are solvent mixtures of water and water-miscible solvents (e.g., tetrahydrofuran and other cyclic ethers, methanol, isopropyl alcohol, and other alcohols). When a solvent mixture of water and a water-miscible solvent is used as the crystallization solvent, the ratio of water to the water-miscible solvent depends on the type of a compound to be crystallized and is, for example, such that the former. (water)/the latter (water-miscible solvent) (by weight) is from about 5/95 to about 95/5 and preferably from about 10/90 to about 80/20.

When the solvent used in the adsorption treatment step and the crystallization solvent are different from each other, the solution should be subjected to solvent replacement. The solvent replacement can be performed by removing the solvent used in the adsorption treatment step by distillation, and adding the crystallization solvent. The removed solvent can be reused.

The amount of the. crystallization solvent depends on the type of the solvent but is generally from about 20 to about 1000 parts by weight, and preferably from about 25 to about 800 parts by weight, relative to 100 parts by weight of the bridged cyclic polycarboxylic acid t-butyl ester. The crystallization operation is often performed by cooling the solution from a temperature ranging from about 30° C. to about 100° C. to a temperature ranging from about −20° C. to about 30° C.

The crystallization operation can efficiently remove, for example, materials and by-products to thereby yield a highly pure bridged cyclic polycarboxylic acid t-butyl ester.

After crystallization, the resulting crystal is rinsed with a solvent to thereby yield a bridged cyclic polycarboxylic acid t-butyl ester with a higher purity. Preferred solvents for use in the rinsing include, for example, solvent mixtures of water and water-miscible solvents (e.g., methanol, ethanol, and other alcohols).

The amount of the solvent (rinsing solvent) for use in rinsing is, for example, from about 10 to about 1000 parts by weight and preferably from about 50 to about 400 parts by weight, relative to 100 parts by weight of the bridged cyclic polycarboxylic acid t-butyl ester. The temperature of the rinsing solvent may be around room temperature but is preferably from about −10° C. to about 10° C.

The crystallized crystal or further rinsed crystal is dried under a condition within a range not deteriorating quality and working efficiency, for example, at a temperature of from about 10° C. to about 100° C. at ambient pressure or under a reduced pressure (under a load) [e.g., from about 0.1 to about 760 mmHg (from about 13.3 to about 101000 Pa)]. The drying operation can be performed under flow of an inert gas such as nitrogen. The solvent can be recovered from a mother liquor obtained by crystallization and washings by distillation or evaporation. The recovered solvent can be reused.

FIG. 1 is a production process chart showing an embodiment of the invented production process. In this embodiment, materials, a bridged cyclic polycarboxylic halide and t-butyl alcohol or its alkali metal salt, and a reaction solvent are fed to reactor 1 (reaction step).

The resulting reaction mixture is transferred from reactor 1 to washing tank 2 and is washed with a washing liquid such as water (washing step). An organic layer after washing generally contains a bridged cyclic polycarboxylic acid t-butyl ester formed by the reaction, trance amounts of by-products and the reaction solvent. An aqueous layer after washing contains, for example, an alkali metal halide.

The washed organic layer is fed to evaporator 3 to thereby remove the reaction solvent by distillation (desolvation step). The bottom product is fed with methanol or another adsorption treatment solvent and an adsorbent to adsorption treatment tank 4 and is subjected to an adsorption treatment (adsorption treatment step). In the adsorption treatment, two or more adsorption techniques can be employed in combination, as described above. When the reaction solvent and the solvent for adsorption treatment are the same, the above operation for the replacement of solvent can be omitted.

The treated solution after adsorption treatment is filtrated through filter 5, and the resulting filtrate is fed to evaporator 6 to thereby remove the adsorption treatment solvent by distillation (desolvation step). In this procedure, the solvent can be easily replaced by adding, among crystallization solvents for use in the subsequent crystallization step, a solvent (crystallization solvent 1) having a boiling point higher than the adsorption treatment solvent to the filtrate, and feeding the resulting mixture to evaporator 6. Another crystallization solvent 2 is added to the bottom product of evaporator 6 according to necessity and is cooled to thereby crystallize a bridged cyclic polycarboxylic acid t-butyl ester (crystallization step). When the adsorption treatment solvent and the crystallization solvent are the same, the operation for the replacement of solvent can be omitted.

The crystallized bridged cyclic polycarboxylic acid t-butyl ester is filtrated through filter 8, is then rinsed with a rinsing solvent (rinsing step), and is dried in vacuum desiccator 9 (drying step) to yield a product. The mother liquor and washings (filtrate) obtained in the crystallization step and rinsing step are fed to evaporator 10 and are recovered from the top (solvent recovering step).

The invented production process can permit the reaction to smoothly proceed to thereby yield a target ester compound in a high yield, in spite of high bulkiness of the materials, the bridged cyclic polycarboxylic halide and t-butyl alcohol or its alkali metal salt. Specifically, when the alkali metal salt of t-butyl alcohol is used, the invented production process can produce the target compound in a vary high yield (e.g., equal to or more-than 90%). The invented production process can therefore commercially efficiently produce bridged cyclic polycarboxylic acid t-butyl esters.

The bridged cyclic polycarboxylic halide represented by Formula (1) for use as the reaction material can be obtained by allowing the bridged cyclic polycarboxylic acid represented by Formula (3) to react with a halogenating agent. This reaction is generally performed in an organic solvent, and such organic solvents include the aforementioned solvents.

Halogenating agents for use in the reaction include, but are not limited to, thionyl chloride, thionyl bromide, and other thionyl halides; phosphoryl chloride, phosphoryl bromide, and other phosphoryl halides; phosphorous trichloride, phosphorous pentachloride, and other phosphorous halides; dichlorotriphenylphosphorane, dibromotriphenylphosphorane, and other halotriphenylphosphoranes; oxalyl chloride, and other oxalyl halides; and other conventional halogenating agents. Among them, preferred halogenating agents are, for example, thionyl chloride and other thionyl halides.

The amount of the halogenating agent is, for example, equal to or more than 1 mole relative to 1 mole of the carboxyl group of the bridged cyclic polycarboxylic acid represented by Formula (3), and the halogenating agent can also be used in large excess.

In this reaction, N,N-dimethylformamide, for example, is preferably used as a reaction accelerator. The amount of the reaction accelerator is from about 0.01 to about 10% by weight, and preferably from about 0.1 to about 5% by weight, relative to the weight of the halogenating agent. The reaction accelerator can be used as a solvent.

The reaction temperature of the halogenation reaction can be appropriately selected depending on, for example, the type of halogenating agent, and generally falls within a range from about −10° C. to about 150° C. The reaction can be performed in any of a batch system, semi-batch system and continuous system.

This reaction can produce the bridged cyclic polycarboxylic halide represented by Formula (1) in a very high yield. The resulting bridged cyclic polycarboxylic halide can be subjected to the desalting reaction as intact or after a simple treatment or purification such as concentration.

In the norbornanepolycarboxylic acid t-butyl ester compounds of the present invention represented by Formula (4), R is a substituent bonded to the norbornane ring. Such substituents include the aforementioned substituents. Among them, preferred substituents are, for example, halogen atoms, $C_1$–$C_4$ alkyl groups, oxo groups, hydroxyl group which may be protected by a protective group, and carboxyl group which may be protected by a protective group.

The numeral n denotes an integer from 0 to 5, and when n is 2 or more, substituents R may be different from each other. The numeral m is an integer equal to or more than 2, is preferably from 2 to 4, and is typically preferably 2.

The bonding site of t-butoxycarbonyl group on the norbornane ring is not specifically limited, but the t-butoxycarbonyl group is preferably bonded at least at the 2-position and 3-position. The norbornanepolycarboxylic acid t-butyl ester compounds each include stereoisomers, and these stereoisomers are all included within the scope of the present invention.

The norbornanepolycarboxylic acid t-butyl ester compound represented by Formula (4) can be obtained in a high yield using the invented process for producing a bridged cyclic polycarboxylic acid t-butyl ester.

This compound has a norbornane ring that is conducive to etching resistance, and has a t-butoxycarbonyl group that can be easily decomposed by action of an acid generated from a photosensitive acid generator to thereby yield a carboxyl group. Accordingly, this compound can be used as a sensitizer, dissolution inhibitor or other additives for photoresists.

Industrial Applicability

The invented process can commercially efficiently produce bridged cyclic polycarboxylic acid t-butyl esters, and can easily produce high quality bridged cyclic polycarboxylic acid t-butyl esters with less impurities such as metallic components.

The present invention provides novel bridged cyclic polycarboxylic acid t-butyl esters that are useful, for example, as sensitizers or dissolution inhibitors for photoresists.

EXAMPLES

The present invention will be illustrated in further detail with reference to several examples below, which are not intended to limit the scope of the invention.

Example 1

In a 3-L round bottom flask equipped with a stirrer, cooling tube, thermometer, and acidic gas trap, 500 g (2.230 mol) of 1,3-adamantanedicarboxylic acid and 1326 g (11.148 mol) of thionyl chloride were placed and were stirred, and to this mixture, 8.15 g (0.112 mol) of N,N-dimethylformamide (DMF) was added dropwise at room temperature, followed by gradual heating and stirring at 70° C. for 2 hours. The reaction mixture was cooled to room temperature, and the remained thionyl chloride and DMF were removed under a reduced pressure to thereby yield 599 g (2.294 mol) of 1,3-adamantanedicarboxylic dichloride as a crudely purified product.

[Spectral data of 1,3-adamantanedicarboxylic dichloride]

$^{13}$C-NMR (500 MHz, CDCl$_3$) δ: 27.7, 34.6, 37.8, 39.9, 178.6

In a 5-L round bottom flask equipped with a stirrer, thermometer, dropping funnel, and calcium chloride tube, 368 g (3.829 mol) of sodium t-butoxide and 1800 ml of toluene were placed, and to this mixture, a solution of 400 g (1.53 mol) of the above-prepared 1,3-adamantanedicarboxylic dichloride in toluene (2400 ml) was added dropwise over 1 hour, with stirring and cooling on ice. The mixture was then raised in temperature to room temperature and was stirred for further 1 hour, followed by washing with distilled water (1000 ml, three times). The resulting mixture was dried over an appropriate amount of sodium sulfate, was filtrated, and the solvent was removed from the filtrate by distillation under a reduced pressure to thereby yield 490 g (1.455 mol) of 1,3-adamantanedicarboxylic di-t-butyl ester represented by the following formula as a white solid matter [purity as determined by gas chromatography: 99%].

The obtained white solid matter was recrystallized from a methanol-water system to thereby yield 460 g (1.369 g) of purified 1,3-adamantanedicarboxylic di-t-butyl ester as a white powder [melting point: 65–66° C.; purity as determined by gas chromatography: 99.5%]

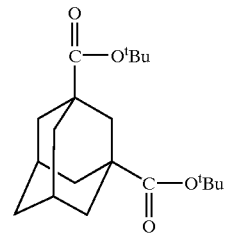

[Spectral data of 1,3-adamantanedicarboxylic di-t-butyl ester]

$^1$H-NMR (500 MHz, CDCl$_3$) δ: 1.43 (s, 18H), 1.60–1.69 (m, 2H), 1.71–1.87 (m, 8H), 1.92 (s, 2H), 2.12 (t, 2H)

Example 2

In a round bottom flask equipped with a stirrer, thermometer, and hydrogen supply line, 10 g of cis-5-norbornene-endo-2,3-dicarboxylic acid, 1 g of a 10% by weight Pd-C, and 25 ml of ethanol were placed and were stirred at room temperature in a hydrogen atmosphere (0.101 MPa) for 3 hours. The resulting reaction mixture was filtrated, and the filtrate was concentrated to thereby yield 9.9 g of cis-norbornane-endo-2,3-dicarboxylic acid in a yield of 98%.

In a round bottom flask equipped with a stirrer, cooling tube, thermometer, and acidic gas trap, 9.9 g of the above-prepared cis-norbornane-endo-2,3-dicarboxylic acid, 42.6 g of thionyl chloride, and 20 ml of toluene were placed and were stirred, and to this mixture, 0.4 g of DMF was added dropwise at room temperature. Next, the resulting mixture was gradually heated and was stirred at 80° C. for 2 hours, followed by cooling to room temperature, and the remained thionyl chloride and DMF were removed therefrom under a reduced pressure to thereby yield 11.7 g of cis-norbornane-endo-2,3-dicarboxylic dichloride in a yield of 99%.

In a round bottom flask equipped with a stirrer, thermometer, dropping funnel, and calcium chloride tube, 12.3 g of sodium t-butoxide and 150 ml of toluene, and to this mixture, a solution of 11.7 g of the above-prepared cis-norbornane-endo-2,3-dicarboxylic dichloride in toluene (150 ml) was added dropwise over 1 hour with stirring and cooling on ice. The resulting mixture was stirred at 10° C. for further 1 hour, and the reaction mixture was washed with distilled water (100 ml, three times), was dried over an appropriate amount of sodium sulfate, was filtrated, followed by the removal of the solvent from the filtrate by distillation under a reduced pressure to thereby yield 12.5 g of cis-norbornane-endo-2 3-dicarboxylic di-t-butyl ester represented-by the following formula in a yield of 92%.

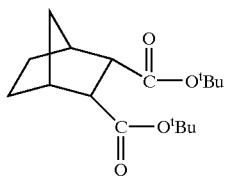

[Spectral data of cis-norbornane-endo-2,3-dicarboxylic di-t-butyl ester]

$^{13}$C-NMR (500 MHz, CDCl$_3$) δ: 26.8, 29.0, 30.9, 32.5, 41.2, 74.0, 176.2

Example 3

A total of 1.68 g (16.6 mmol) of triethylamine was added to a toluene solution (30 ml) of 2.0 g (7.56 mmol) of 1,3-adamantanedicarboxylic acid dichloride obtained in the same manner as in Example 1, and to this mixture, 1.12 g (15.1 mmol) of t-butyl alcohol was added dropwise over 10 minutes, followed by stirring at room temperature for 2 hours. The reaction mixture was washed with distilled water (15 ml, three times), was dried over sodium sulfate, was filtrated, and the solvent was removed from the filtrate by distillation under a reduced pressure to yield a concentrate, and the concentrate was subjected to column chromatography on a silica gel to thereby yield 0.77 g (2.77 mmol) of 1,3-adamantanedicarboxylic di-t-butyl ester as a white solid matter.

Example 4

Adamantane-1,3-dicarboxylic acid di-t-butyl ester was prepared according to the production process chart of FIG. 1.

In 10-L glass reactor 1, 300 g of adamantane-1,3-dicarboxylic acid, 4.8 g of N,N-dimethylformamide, and 2100 g of toluene were placed, and to this mixture, 331.5 g of thionyl chloride was added dropwise in a nitrogen atmosphere over 1 hour. The resulting mixture was aged for 1 hour, followed by dropwise addition of a mixture of 446 g of t-butyl potassium and 2100 g of toluene over 3 hours. After 1-hour aging, the reaction was completed. During the reaction, the temperature of the reaction mixture was controlled at 30° C. The reaction mixture was analyzed by gas chromatography to find that 380 g of adamantane-1,3-dicarboxylic acid di-t-butyl ester was formed.

This reaction mixture was transferred to washing tank 2 equipped with a stirrer, and was washed with water three times at a temperature of 30° C. In each washing operation, 60 parts by weight of a washing liquid (water) was used relative to 100 parts by weight of the reaction mixture to be washed. This washing operation yielded a toluene solution of adamantane-1,3-dicarboxylic acid di-t-butyl ester as an organic layer.

The organic layer was concentrated using 10-L glass evaporator 3 [50 mmHg (6664 Pa), 60° C.] to thereby yield 433.5 g of a concentrate.

A total of 1465 g of methanol was added to the above-prepared concentrate, and to the resulting mixture, 515 g of water was added under reflux, and the mixture was stirred and cooled on ice for 3 hours to crystallize adamantane-1,3-dicarboxylic acid di-t-butyl ester to thereby yield a slurry. The slurry had a temperature of 2° C. After the completion of crystallization, the crystal was separated by filtration, and the separated crystal was washed with 500 g of a cool 50% by weight methanol aqueous solution. After the completion of washing, the washed crystal was separated by filtration and was dried in a vacuum desiccator for 24 hours [10 mmHg (1330 Pa), 50° C.] to thereby yield 370.5 g of white adamantane-1,3-dicarboxylic acid di-t-butyl ester. The obtained adamantane-1,3-dicarboxylic acid di-t-butyl ester had a purity of 99.9% by weight.

Example 5

Adamantane-1,3-dicarboxylic acid di-t-butyl ester was prepared according to the production process chart of FIG. 1.

In 10-L glass reactor 1, 300 g adamantane-1,3-dicarboxylic acid, 4.8 g of N,N-dimethylformamide, and 2100 g of toluene were placed, followed by dropwise addition of 331.5 g of thionyl chloride in a nitrogen atmosphere over 1 hour. The resulting mixture was aged for 1 hour, followed by dropwise addition of a mixture of 446 g of t-butyl potassium and 2100 g of toluene over 3 hours. After 1-hour aging, the reaction was completed. During the reaction, the temperature of the reaction mixture was controlled at 30° C. The reaction mixture was analyzed by gas chromatography to find that 380 g of adamantane-1,3-dicarboxylic acid di-t-butyl ester was formed.

This reaction mixture was transferred to washing tank 2 equipped with a stirrer, and was washed with water three times at a temperature of 30° C. In each washing operation, 60 parts by weight of a washing liquid (water) was used relative to 100 parts by weight of the reaction mixture to be washed. This washing process yielded a toluene solution of adamantane-1,3-dicarboxylic acid di-t-butyl ester as an organic layer.

The organic layer was concentrated using 10-L glass evaporator 3 [50 mmHg (6664 Pa), 60° C.] to thereby yield 433.5 g of a concentrate.

A total of 1465 g of methanol was added to the above-prepared concentrate. To the resulting solution, 70.2 g of a chelest resin (available from Mitsubishi Chemical Corporation, under the trade name of "CR-11") to perform adsorption treatment at a temperature of 40° C. Subsequently, the chelest resin was removed by filtration through filter 5.

The filtrate was heated and 515 g of water was added to the filtrate under reflux, followed by stirring and cooling on ice for 3 hours to crystallize adamantane-1,3-dicarboxylic acid di-t-butyl ester to thereby yield a slurry. The slurry had a temperature of 2° C. After the completion of crystallization, the crystal was separated by filtration, followed by washing with 500 g of a cool 50% by weight methanol aqueous solution. After the completion of washing, the washed crystal was separated by filtration and was dried in a vacuum desiccator for 24 hours [10 mmHg (1330 Pa), 50° C.] to thereby yield 370.5 g of white adamantane-1,3-dicarboxylic acid di-t-butyl ester. The obtained adamantane-1,3-dicarboxylic acid di-t-butyl ester had a purity of 99.9% by weight and an Fe content, as a metallic component of impurity, of 63 ppb by weight.

What is claimed is:

1. A process for producing a bridged cyclic polycarboxylic acid t-butyl ester, said process comprising at least a reaction step of allowing a bridged cyclic polycarboxylic halide represented by following Formula (1):

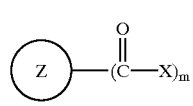

(1)

(wherein ring Z is a bridged cyclic carbon ring; X is a halogen atom; and m denotes an integer of equal to or more than 2, where ring Z may have a substituent) to react with t-butyl alcohol or its alkali metal salt to thereby yield an ester represented by following Formula (2):

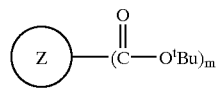

(2)

(wherein ᵗBu denotes a t-butyl group; and ring Z and m have the same meanings as defined above), and an adsorption treatment step of subjecting a reaction product of the bridged cyclic polycarboxylic halide with t-butyl alcohol or its alkali metal salt to an adsorption treatment with an adsorbent to purify the ester.

2. A process for producing a bridged cyclic polycarboxylic acid t-butyl ester, said process comprising at least a reaction step wherein a bridged cyclic polycarboxylic acid represented by following Formula (3):

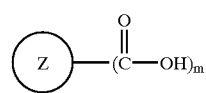

(3)

(wherein ring z is a bridge cyclic carbon ring; and m denotes an integer or equal to or more than 2, where ring Z may have a substituent) is allowed to react with a halogenating agent to thereby yield a bridged cyclic polycarboxylic halide represented by following Formula (1):

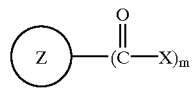

(1)

(wherein X is a halogen atom; and ring Z and m have the same meanings as defined above), and said bridged cyclic polycarboxylic halide is allowed to react with t-butyl alcohol or its alkali metal salt to thereby yield an ester represented by following Formula (2):

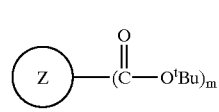

(2)

(wherein ᵗBu denotes a t-butyl group; and ring Z and m have the same meanings as defined above), and an adsorption treatment step of subjecting a reaction product of the bridged cyclic polycarboxylic halide with t-butyl alcohol or its alkali metal salt to an adsorption treatment with an adsorbent to purify the ester.

3. The process for producing a bridged cyclic polycarboxylic acid t-butyl ester according to claim 1, said process comprising a reaction step of allowing a bridged cyclic polycarboxylic halide represented by Formula (1) with t-butyl alcohol or its alkali metal salt to thereby yield the ester represented by Formula (2), and a purification step wherein the reaction product of the bridged cyclic polycarboxylic halide with t-butyl alcohol or its alkali metal salt is successively subjected to (A) a washing step of washing the reaction product with water, (B) an adsorption treatment step of subjecting the reaction product to an adsorption treatment with an adsorbent, and (C) a crystallization step to thereby yield a purified bridged cyclic polycarboxylic acid t-butyl ester.

4. The process for producing a bridged cyclic polycarboxylic acid t-butyl ester according to any one of claims 1, 2 and 3, wherein ring Z in Formula (1) is a bicyclic, tricyclic or tetracyclic bridged cyclic carbon ring.

5. The process for producing a bridged cyclic polycarboxylic acid t-butyl ester according to any one of claims 1, 2 and 3, wherein ring Z in Formula (1) is an adamantine ring or a norbornane ring.

6. A norbornanepolycarboxylic acid t-butyl ester compound represented by following formula (4):

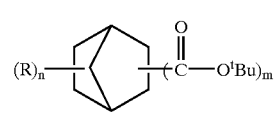

(4)

(wherein R is a substituent bonded to norbornane ring; n denotes an integer from 0 to 5, where substituents R may be different from each other when n is equal to or more than 2; ᵗBu denotes a t-butyl group; and m denotes an integer equal to or more than 2.).

* * * * *